(12) United States Patent
Lu et al.

(10) Patent No.: US 8,450,073 B2
(45) Date of Patent: May 28, 2013

(54) STABILIZING AGENTS AND CAPTURE LIGANDS FOR USE IN ASSAYS MEASURING ANALYTE CONCENTRATIONS

(75) Inventors: Wenyuan Lu, Chaska, MN (US); Katherine M. Leith, Minnetonka, MN (US); Stephen P. Chan, Minneapolis, MN (US); Courtney E. Walton, Savage, MN (US)

(73) Assignee: Beckman Coulter, Inc., Brea, CA (US)

( * ) Notice: Subject to any disclaimer, the term of this patent is extended or adjusted under 35 U.S.C. 154(b) by 133 days.

(21) Appl. No.: 12/964,940

(22) Filed: Dec. 10, 2010

(65) Prior Publication Data
US 2011/0091909 A1    Apr. 21, 2011

Related U.S. Application Data

(62) Division of application No. 11/878,121, filed on Jul. 20, 2007, now Pat. No. 7,897,352.

(60) Provisional application No. 60/833,786, filed on Jul. 28, 2006.

(51) Int. Cl.
*G01N 33/53* (2006.01)
*G01N 33/543* (2006.01)
*C07K 16/00* (2006.01)

(52) U.S. Cl.
CPC .............. *G01N 33/53* (2013.01); *G01N 33/543* (2013.01); *C07K 16/00* (2013.01)

USPC ............ 435/7.1; 435/7.5; 435/7.93; 436/523; 436/526; 530/389.8

(58) Field of Classification Search
None
See application file for complete search history.

(56) References Cited

U.S. PATENT DOCUMENTS 5,478,741 A * 12/1995 Maret et al. .................... 435/342
6,090,571 A * 7/2000 Akhavan-Tafti et al. ....... 435/21

FOREIGN PATENT DOCUMENTS

| EP | 240021 A1 | * | 10/1987 |
| EP | 1207393 A1 | * | 5/2002 |
| WO | WO 0107913 A1 | * | 2/2001 |

OTHER PUBLICATIONS

Richardson et al. The use of coated paramagnetic particles as a physical label in magneto-immunoassay. Bioscience & Bioelectronics 2001, col. 16, pp. 989-993.*

Oellerich. Enzyme immunoassay, A review. 1984, vol. 22, pp. 895-904.*

* cited by examiner

*Primary Examiner* — Shafiqul Haq
(74) *Attorney, Agent, or Firm* — Richard S. Handley; Anne M. Murphy

(57) ABSTRACT

The present invention is related to compositions useful for the measurement of free or unbound analyte concentrations in a fluid. The present invention includes the use of capture ligands and stabilizing agents to improve the accuracy of analyte concentration assays. Methods and tools for using the present invention are also disclosed.

11 Claims, 7 Drawing Sheets

FIG. 1: Various R groups for forming stabilizing agents comprising the general formula RX.

R GROUP

| Category | Chemical Groups Such As |
|---|---|
| I. Alkyl or aryl | Straight and branched alkyl and aryl<br>Olefin homologs with one or more unsaturated carbon to carbon bond(s)<br>Cyclic and poly-cyclic derivatives of alkyl and aryl<br>Heterocyclic derivatives of alkyl and aryl<br>Derivatives of alkyl and aryl with halogen, Si, O, N, and/or P<br>Hydroxy, ester, ether, carboxy, amine, amine oxide and amide derivatives of alkyl and aryl<br>Phosphate, acetate, carboxylate, and ammonium derivatives of alkyl and aryl<br>Anionic, cationic, and non-ionic derivatives of alkyl and aryl<br>Derivatives of alkyl and aryl |
| II. Fatty acid | Fatty acids and homologs<br>Esters of fatty acid<br>Alkanoamide derivatives of fatty acids<br>Oxyethylated fatty acid<br>Non-ionic, anionic, and cationic derivatives of fatty acids<br>Derivatives of fatty acid with halogen, Si, O, N, and/or P<br>Derivatives of fatty acids |
| III. Alcohol | Alcohols<br>Alkyl phenol and derivatives<br>Esters of alcohols<br>Derivatives of alcohols and phenols with halogen, Si, O, N, and/or P<br>Hydrocarbon derivatives of alcohols |
| IV. Ester | Esters, polyesters, sorbitan esters, sugar esters<br>Hydrocarbon derivatives of esters<br>Anionic, cationic, and non-ionic derivatives of esters<br>Derivatives of esters |
| V. Ether | Hydrocarbon groups comprising an ether bond<br>Anionic, cationic, and non-ionic ether derivatives<br>Ether derivatives<br>Polyethers, phenol ethers, crown ethers |
| VI. Amine | Polyamines, amine oxides, amine ethoxylates and other amine derivatives |
| VII. Oxyalkylate | Polyoxyethylene, polyoxypropylene, polybutylene, and related structures as well as their block copolymers<br>Oxyalkylated derivatives with hydrocarbon chain<br>Oxyethylated copolymers with other organic or in-organic moieties<br>Oxyalkylated derivatives and co-polymers with halogen, O, N, and/or P<br>Cationic, anionic, non-ionic derivatives of oxyalkylated moieties |
| VIII. Siloxane | Straight, branched, and cyclic siloxane<br>Chemical structures with carbosilane backbone<br>Siloxane and carbosilane backbones with hydrocarbon side chains<br>Copolymers of silicone with polyether, polyester, polyol, polyamine, polyurethane, and other polymeric moieties<br>Organosilicones<br>Ammonium salt of siloxanes and carbosilanes<br>Cationic, anionic, and non-ionic derivatives of siloxane and carbosilane<br>Anionic, cationic, and non-ionic derivatives of siloxanes<br>Derivatives of siloxanes |

FIG. 2: The X groups for forming stabilizing agents comprising the general formula RX.

| X GROUP | |
|---|---|
| Category | Chemical Groups Such As: |
| I. A group containing sulfur | Sulfate, sulfonic acid, sulfonate, sulfite, sulfoxide (-SO, -SO$_2$), taurate, sulfosuccinate, sulfobetaine, sulfatobetaine, sulfonamide, methoxymethanilamide, or other functional groups that contain sulfate, sulfonate, and sulfonic acid |
| II. A group containing a halogen | Chlorite, chloride, chlorine, iodide, iodate, iodine, bromide, bromine, fluorine, or fluoride |
| III. A group containing nitrogen | Nitrate, nitrite, amide, amine, or amine derivative (e.g. quaternary amine) |
| IV. A group containing phosphorus | Phosphate, phosphite, or other reduced forms of phosphate |
| V. A group containing carbon | Carboxylate, acrylate, sebacate, phthalate or acetate |
| VI. A group containing oxygen | Oxide |
| VII. A group containing boron | Borate |
| VIII. A group containing silicon | Silane, or silicate |

FIG. 3: Chart illustrating various RX chemicals evaluated as stabilizing agents disclosed in the present invention

| Trade Name | Sulfate/sulfonate | Working conc V/V% * | Chemical names | Tail | Head |
|---|---|---|---|---|---|
| Aerosol OT | Yes | 0.05% | Sodium dioctylsulfosuccinate | C8 (2) | Sulfosuccinate |
| Alkamuls 719 | No | None | PEG-30 caster oil | C18 (9-ene, 12-OH) | POE(30) |
| Alkamuls EL 620 | No | None | PEG-40 caster oil | C18 (9-ene, 12-OH) | POE (40) |
| Benzalkonium Chloride | No | None | Benzalkonium (C8-C18) chloride | Benzalkyl C8-18 | Amine |
| BioTerge AS40 | Yes | 0.1 | Sodium olefin (C14 -16) sulfonate | C14-16 | Sulfonate |
| Brij 30 | No | None | Polyoxyethylene(4) lauryl ether | C12 | POE(4) |
| Brij 35 | No | None | Polyoxyethylene(23) dodecyl ether | C12 | POE(23) |
| Brij 700 | No | None | Polyoxyethylene(100) stearyl ether | C18 (9-ene, 12-OH) | POE(100) |
| Brij 92 | No | None | Polyoxyethylene(2) oleyl ether | C18 (9-ene) | POE(2) |
| Brij 98 | No | None | Polyoxyethylene(2) oleyl ether | C18 (9-ene) | POE(20) |
| Chemal BP-264 | No | None | Alkoxylated block copolymer | PPO(30) | POE(75) X2 |
| Chemal LA-9 | No | None | Polyoxyethylene(9) lauryl alcohol | C12 | POE(9) |
| Cremophor EL | No | None | Polyoxyethylated(35) castor oil | C18(9-ene, 12-OH) | POE |
| Eluent | No | None | Alkylglucosides | Alkylmixture | Glucose |
| Empigen BB | No | None | N-dodecyl-N,N-dimethylglycine | C12 | Dimethylglycine |
| FC100 (as control) | Yes | 0.2 | (see Paragraph [0004]) | | |
| FC1100 | Yes | 0.5 | (a purer form of FC100 from 3M) | | |
| Forafac 1157 | No | None | Perfluoroalkyl betaine | Fluorocarbon (C6) | Betaine |
| Geropon T77 | Yes | 0.1 | N-oleyl-N-methyltaurate, Na salt | C18(9-ene) | Taurate |
| Igepal CA210 | No | Insol | Polyoxyethylene(2) isooctylphenyl ether | C8-phenol | POE(2) |
| Myrj 45 | No | Insol | Polyoxyethylene(8) stearate | C18 | POE(8) |
| Myrj 52 | No | None | Polyoxyethylene(40) stearate | C18 | POE(40) |
| Myrj 53 | No | None | Polyoxyethylene(50) stearate | C18 | POE(50) |
| Myrj 59 | No | None | Polyoxyethylene(100) stearate | C18 | POE(100) |
| Na Cholate | No | None | Sodium cholate | Steroid | Cholate |
| Na deoxycholate | No | None | Sodium deoxycholate | Steroid | Deoxycholate |
| Ninate 411 | Yes | None, insoluble | Amine alkylbenzene sulfonate | alkylbenzene | sulfonate |
| Pluronic 17R4 | No | None | Poly(oxyethylene-co-oxypropylene) block copolymer | PPO (ca. 3000) | POE |
| Pluronic F108 | No | None | Poly(oxyethylene-co-oxypropylene) block copolymer | PPO (54) | POE 80% |

FIG. 3: Chart illustrating various RX chemicals evaluated as stabilizing agents disclosed in the present invention

| Trade Name | Sulfate/sulfonate | Working conc V/V% * | Chemical names | Tail | Head |
|---|---|---|---|---|---|
| Pluronic F127 | No | None | Poly(oxyethylene-co-oxypropylene) block copolymer | PPO (ca. 3600, 1800) | POE 70% |
| Pluronic F68 | No | None | Poly(oxyethylene-co-oxypropylene) block copolymer | PPO (30) | POE(75) X2 |
| Pluronic F88 | No | None | Poly(oxyethylene-co-oxypropylene) block copolymer | PPO (ca. 3000, 2400) | POE |
| Pluronic L121 | No | Insoluble | Poly(oxyethylene-co-oxypropylene) block copolymer | PPO (ca. 3600) | POE 10% |
| Pluronic L31 | No | None | Poly(oxyethylene-co-oxypropylene) block copolymer | PPO (ca. 900) | POE 10% |
| Pluronic L43 | No | None | Poly(oxyethylene-co-oxypropylene) block copolymer | PPO | POE |
| Pluronic L44 | No | None | Poly(oxyethylene-co-oxypropylene) block copolymer | PPO | POE |
| Pluronic L 62 | No | None | Poly(oxyethylene-co-oxypropylene) block copolymer | PPO (ca. 1800, 30) | POE(7) x2 |
| Pluronic L64 | No | None | Poly(oxyethylene-co-oxypropylene) block copolymer | PPO (30) | POE 40% |
| Pluronic P65 | No | None | Poly(oxyethylene-co-oxypropylene) block copolymer | PPO | POE |
| Pluronic P105 | No | None | Poly(oxyethylene-co-oxypropylene) block copolymer | PPO (54) | POE 50% |
| Rhodamox LO | No | None | Lauramine oxide | C12 | N-oxide |
| Rhodapon BOS (= EHS) | Yes | 0.05 | 2-ethylhexyl sulfate, Na | C6(2-C2) | Sulfate |
| Rhodasurf ON-780 | No | None | Polyethoxylated(20) oleyl alcohol | C18 (9-ene) | POE(20) |
| Sodium dodecyl sulfate | Yes | 0.1 | Sodium dodecyl sulfate | C12 | Sulfate |
| Silwet L7600 | No | None | Polydimethylsiloxane methylethoxylate | Dimethylsiloxane | Methylethoxylate |
| Span 60 | No | Insol | Sorbitan monostearate | C18 | Sorbitan |
| Standapol ES-1 | Yes | 0.1 | Sodium polyoxyethylene(1) lauryl sulfate | C12 | POE, sulfate |
| Surfactant 10G | No | None | P-isononylphenoxypoly(glycidol) | C9-phenol | PPO |
| Surfynol 465 | No | None | 2,4,7,9-tetramethyl-5-decyne-4,7-diol ethoxylate (10) | C10(5-yne, branched) | POE(10) |
| Surfynol 485 | No | None | 2,4,7,9-tetramethyl-5-decyne-4,7-diol | C10(5-yne, branched) | POE(30) |

FIG. 3: Chart illustrating various RX chemicals evaluated as stabilizing agents disclosed in the present invention

| Trade Name | Sulfate/sulfonate | Working conc V/V%* | Chemical names | Tail | Head |
|---|---|---|---|---|---|
| Tetronic 1307 | No | None | Ethylenediamine alkoxylate block copolymer ethoxylate (30) | PPO | POE |
| Tetronic 17R4 | No | None | Ethylenediamine alkoxylate block copolymer | PPO | POE |
| Tetronic 701 | No | Insol | Ethylenediamine alkoxylate block copolymer | PPO | POE |
| Tetronic 904 | No | None | Ethylenediamine alkoxylate block copolymer | PPO | POE |
| Tetronic 90R4 | No | None | Ethylenediamine alkoxylate block copolymer | PPO | POE |
| Triton X100 | No | None | Octylphenoxypolyethoxy(9-10)ethanol | C8-phenol | POE(9-10) |
| Triton X305 | No | None | Octylphenoxypolyethoxy(30)ethanol | C8-phenol | POE(30) |
| Triton X45 | No | None | Octylphenoxypolyethoxy(5)ethanol | C8-phenol | POE(5) |
| Tween 20 | No | None | Polyoxyethylene(20)sorbitan monolaurate | C12 | POE(20) sorbitan |
| Tween 40 | No | None | Polyoxyethylene(20)sorbitan monopalmitate | C16 | POE(20) sorbitan |
| Tween 60 | No | None | Polyoxyethylene(20)sorbitan monostearate | C18 | POE(20) sorbitan |
| Tween 65 | No | Insol | Polyoxyethylene(20)sorbitan tristearate | C18 x3 | POE(20) sorbitan |
| Tween 80 | No | None | Polyoxyethylene(20)sorbitan monooleate | C18 (9-ene) | POE(20) sorbitan |
| Tween 85 | No | Insol | Polyoxyethylene(20)sorbitan trioleate | C18 (9-ene) x3 | POE(20) sorbitan |
| Zonyl FS300 | Yes | None | Non-ionic fluorocarbon | Fluorocarbon (C6) | POE |
| Zonyl FS62 | Yes | 0.05 | $F(CF_2)_6$-$(CH_2)_2$-$SO_3$ (H, $NH_4$) | Fluorocarbon (C6) | Sulfonate |
| Zonyl FSK | No | None | Polytetrafluoroethylene acetoxypropyl betaine | Fluorocarbon | Betaine |
| Zonyl FSN | No | None | $F(CF_2CF_2)_{1-9}CH_2CH_2O(CH_2CH_2)_{[0-25]}H$ | Fluorocarbon C2-C18 | POE(1-26) |
| Zonyl FSO | No | None | $F(CF_2CF_2)_{1-7}CH_2CH_2O(CH_2CH_2)_{[0-15]}H$ | Fluorocarbon C2-C14 | POE(1-16) |
| Zonyl TBS | Yes | 0.1 | $F(CF_2CF_2)_{3-8}(CH_2)_2$-$SO_3$ (H, $NH_4$) | Fluorocarbon (C6-C16) | Sulfonate |
| Zwittergent 3-08* | No | None | N-octyl-N,N-dimethyl-3-amino-1-propanesulfonate | C8 | Sulfobetaine |

FIG. 3: Chart illustrating various RX chemicals evaluated as stabilizing agents disclosed in the present invention

| Trade Name | Sulfate/sulfonate | Working conc V/V% * | Chemical names | Tail | Head |
|---|---|---|---|---|---|
| Zwittergent 3-10* | No | None | N-decyl-N,N-dimethyl-3-amino-1-propanesulfonate | C10 | Sulfobetaine |
| zwittergent 3-12* | No | None | N-dodecyl-N,N-dimethyl-3-amino-1-propanesulfonate | C12 | Sulfobetaine |
| Zwittergent 3-14* | No | None | N-tetradecyl-N,N-dimethyl-3-amino-1-propanesulfonate | C14 | Sulfobetaine |
| Zwittergent 3-16* | No | Insol | N-hexadecyl-N,N-dimethyl-3-amino-1-propanesulfonate | C16 | Sulfobetaine |

* These concentrations are the concentrations in Vial Reagent F.

FIG. 4: Chart illustrating various EHS homologs evaluated as stabilizing agents disclosed in the present invention

| Chemical names | Sulfate/sulfonate | Working conc V/V% ** | Tail | Head |
|---|---|---|---|---|
| Potassium sulfate | Yes | None | None | Sulfate |
| Butyl sulfonate | Yes | None | Butyl | Sulfonate |
| Benzylsulfonate | Yes | None | Benzyl | Sulfonate |
| 1-pentanesulfonic acid, Na salt | Yes | 1% | Pentyl | Sulfonate |
| 1-hexanesulfonic acid, Na salt | Yes | 1% | Hexyl | Sulfonate |
| 1-heptanesulfonic acid, Na salt | Yes | 1% | Heptyl | Sulfonate |
| 1-octanesulfonic acid, Na salt | Yes | 1% | Octyl | Sulfonate |
| 1-decanesulfonic acid, Na salt | Yes | None: Insoluble at both 0.5% and 1% | Dodecyl | Sulfonate |

** These concentrations are the concentrations in Vial Reagent F.

STABILIZING AGENTS AND CAPTURE LIGANDS FOR USE IN ASSAYS MEASURING ANALYTE CONCENTRATIONS

CROSS REFERENCE TO RELATED APPLICATION

This application is a Divisional Application of U.S. patent application Ser. No. 11/878,121 filed on Jul. 20, 2007, which claims priority from U.S. provisional application Ser. No. 60/833,786 filed on Dec. 28, 2006.

BACKGROUND OF THE INVENTION

1. Field of the Invention

The present invention teaches new and useful compositions for the measurement of free or unbound analyte concentrations in a fluid. The present invention includes the use of capture ligands and stabilizing agents to improve the accuracy of analyte concentration assays. Methods and tools for using the present invention are also disclosed.

2. Background Art

Various assays have been developed to measure the concentration of an analyte in solution. For example, assays have included mixing a solution containing an analyte with a capture ligand, washing away any impurities, and then measuring the analyte associated with the capture ligand. Several technical difficulties exist with these detection methods. In some instances, unintended binding of impurities to the capture ligand occurs. Additionally, in some instances the binding of the analyte to the capture ligand is not stable and the analyte disassociates from the ligand. In some instances, the analyte in a solution can exist in a bound form (e.g., bound to a protein) and an unbound form, and it may be desirable to only measure the concentration of the unbound form. Thus, in some instances it is necessary to stabilize the equilibrium between bound and unbound forms in order to obtain an accurate and reproducible measurement of analyte concentration.

To address these problems, Beckman Coulter, Incorporated (BCI, Fullerton Calif.) has traditionally used an alkyl amine fluoro-surfactant (FC100, manufactured by 3M Corporation, St. Paul, Minn.) in BCI's various analyte concentration assays. FC100 is a complex cocktail of amine fluoro-surfactants that exhibits substantial lot to lot variability in its exact chemical composition. According to 3M Corporation's Material Safety Data Sheet (MSDS, issued Feb. 8, 2000, Document Number 10-3799-3), FC100 contains water, diethylene glycol butyl ether, fluoroalkyl sulfonate sodium salt, and a trade secret mixture of residual organic fluorochemicals. Without being limited by theory, the inventors believe that an alkyl amine fluoro-surfactant facilitates the accurate determination of the amount of free unbound analyte versus bound analyte present in a sample solution by stabilizing the equilibrium and therefore allowing for accurate measurement of analyte concentration.

Several years ago, the Environmental Protection Agency of the United States expressed concern regarding certain fluorocarbon compounds, such as fluorocarbon octanoic acid and its derivatives, as potentially hazardous compounds. Therefore, a need exists for an alternative to replace the alkyl amine fluoro-surfactant with a different assay composition that can function in determining analyte concentration.

The present invention provides novel compositions as well as methods and kits for using those compositions in assays to accurately measure the free unbound analyte in a sample from a subject.

BRIEF SUMMARY OF THE INVENTION

The present invention addresses the needs mentioned above and the problems encountered with currently available technologies.

The present invention is directed to methods for measuring a concentration of free analyte, the methods comprising:
  (a) adding a capture ligand to a vessel;
  (b) adding a stabilizing agent to the vessel;
  (c) adding a sample comprising the free analyte to the vessel;
  (d) adding a detection system to the vessel; and
  (e) measuring the concentration of the free analyte in the sample using the detection system.

The present invention is also directed to compositions for use in an assay measuring the concentration of a free analyte, the compositions comprising a capture ligand for the free analyte, and a stabilizing agent, with the proviso that the stabilizing agent does not comprise an alkyl amine fluoro-surfactant.

The present invention is also directed to kits for use in estimating a concentration of a free analyte, the kits comprising:
  (a) a capture ligand for the analyte;
  (b) a stabilizing agent; and
  (c) a detection system.

In some embodiments, the kit can further comprise (d) a reference standard.

The present invention is also directed to stabilizing agents comprising the general formula RX, wherein R and X are covalently bound, and wherein R is a saturated or unsaturated alkyl, alkoxy, alkoxyalkyl, alkoxyalkoxyalkyl, alkylaminoalkyl, alkylaminooxyalkyl, alkoxyaminoalkyl, phosphonoalkyl, carboxyalkyl, carboxyalkoxyalkyl, carboxyalkylaminoalkyl, carboxyalkylamidoalkyl, cycloalkyl, cycloalkylallyl, heterocycloalkylalkyl, heterocyclyl, aryl, arylalkyl, heteroaryl, heteroarylalkyl, siloxane, or carbosilane, any of which can be optionally interrupted with one or more oxygen, nitrogen, phosphorous, or silicon atoms, and wherein any one of the R substitutents can be optionally substituted with one or more hydroxy, carbonyl, halogen, phosphate, acetyl, ammonium, or combinations thereof, and wherein X is sulfate, sulfonic acid, sulfonate, sulfite, taurate, sulfosuccinate, sulfobetaine, sulfonamide, methoxymethanilamide, sulfamyl, sulfeno, chlorite, chloride, iodide, iodate, bromide, bromate, fluoride, fluorate, nitrate, nitrite, nitroamine, amino, imino, isocyanoto, isothiocyano, acetamido, acetimido, azido, diazo, cyano, cyanato, phosphate, phospho, phosphono, phosphinyl, phosphino, carboxylate, acrylate, sebacate, phthalate, acetate, oxide, borate, peroxoborate, tetraborate, boranate, silane, orthosilcate, metasilicate, or a metal silicate, with the proviso that RX cannot be an alkyl amine fluoro-surfactant. FIGS. 1 and 2 describe stabilizing agents comprising the general formula RX.

In some embodiments, R can be alkyl, alkylene, alkyne, alkoxyalkyl, alkoxyalkoxyalkyl, alkylaminoalkyl, alkylaminooxyalkyl, alkoxyaminoalkyl, phosphonoalkyl, carboxyalkyl, carboxyalkoxyalkyl, wherein any one of which is optionally substituted with one or more hydroxy, carbonyl, halogen, phosphate, acetyl, ammonium, or combinations thereof.

In some embodiments, R can be propyl, isopropyl, butyl, isobutyl, pentyl, hexyl, heptyl, octyl, 2-methyl butyl, 2-ethyl butyl, 2-propyl butyl, 3-methyl butyl, 3-ethyl butyl, 3-propyl pentyl, 2-methyl pentyl, 2-ethyl pentyl, 2-propyl pentyl, 3-methyl pentyl, 3-ethyl pentyl, 3-propyl pentyl, 4-methyl pentyl, 4-ethyl pentyl, 4-propyl pentyl, 2-methyl hexyl, 2-ethyl hexyl, 2-propyl hexyl, 3-methyl hexyl, 3-ethyl hexyl, 3-propyl hexyl, 4-methyl hexyl, 4-ethyl hexyl, 4-propyl hexyl, 5-methyl hexyl, 5-ethyl hexyl, 5-propyl hexyl, 2-methyl heptyl, 2-ethyl heptyl, 2-propyl heptyl, 3-methyl heptyl, 3-ethyl heptyl, 3-propyl heptyl, 4-methyl heptyl, 4-ethyl heptyl, 4-propyl heptyl, 5-methyl heptyl, 5-ethyl heptyl, 5-propyl heptyl, 6-methyl heptyl, 6-ethyl heptyl, 6-propyl heptyl, 2-methyl octyl, 2-ethyl octyl, 2-propyl octyl, 3-methyl octyl, 3-ethyl octyl, 3-propyl octyl, 4-methyl octyl, 4-ethyl octyl, 4-propyl octyl, 5-methyl octyl, 5-ethyl octyl, 5-propyl octyl, 6-methyl octyl, 6-ethyl octyl, 6-propyl octyl, any of which can be optionally substituted with one or more hydroxy, carbonyl, halogen, phosphate, acetyl, ammonium, or combinations thereof.

In some embodiments, X can be a sulfate, sulfonic acid, sulfonate, sulfite, taurate, sulfosuccinate, sulfobetaine, sulfonamide, methoxymethanilamide, sulfamyl, or sulfeno, preferably sulfate, sulfonic acid, sulfosuccinate, or taurate.

In some embodiments, R is $C_{6-18}$ alkyl and X is sulfate, sulfonate or sulfonic acid. In some embodiments, the stabilizing agent is selected from the group consisting of 2-ethyl-hexyl sulfate; 1-hexane sulfonic acid, or salt thereof; 1-heptane sulfonic acid, or salt thereof; 1-octane sulfonic acid, or salt thereof; 1-decane sulfonic acid, or salt thereof; sodium $C_{14-16}$ olefin sulfonate; sodium dodecyl sulfate; sodium dioctyl sulfosuccinate; sodium N-oleyl-N-methyltaurate; sodium polyoxyethylene lauryl sulfate; amine alkylbenzyl sulfonate; sodium ethyl-hexyl sulfate; and combinations thereof. In some embodiments, the stabilizing agent is 2-ethyl-hexyl sulfate. In some embodiments, the composition comprises a salt of the stabilizing agent.

In some embodiments, the analyte is a hormone, drug, or vitamin. In some embodiments, the analyte comprises a single enantiomer or a de-iodinated form of the analyte.

In some embodiments, the capture ligand and the stabilizing agent are combined in a manner that maintains the equilibrium between free analyte and bound analyte in a sample to be analyzed.

In some embodiments, a volume fraction of the stabilizing agent is about 0.0001 to about 0.1 volume percent.

In some embodiments, a concentration of the stabilizing agent is about 5 to about 750 micromolar.

In some embodiments, a volume fraction of the 2-ethyl-hexyl sulfate is about 0.004 to about 0.015 volume percent.

In some embodiments, a concentration of the 2-ethyl-hexyl sulfate is about 75 to about 650 micromolar.

In some embodiments, the capture ligand is selected from the group consisting of an antibody, antibody fragment, antibody mimic, or analyte-specific binding protein such as intrinsic factor or folate-binding protein. In some embodiments, the capture ligand is immobilized on a solid phase. In some embodiments, the capture ligand is an analyte-specific binding protein. In some embodiments, the capture ligand is an antibody.

In some embodiments, the analyte is a thyroid hormone.

In some embodiments, the present invention further comprises an immunoassay system. In some embodiments, an immunoassay system comprises paramagnetic particles coated with a biotin-specific binding molecule, a biotinylated analyte-specific capture protein, or a combination thereof.

In some embodiments, the immunoassay system comprises a detectable label.

BRIEF DESCRIPTION OF THE FIGURES

FIG. 1 is a chart illustrating various R groups (I through VIII) for forming the stabilizing agents disclosed in the present invention.

FIG. 2 is a chart illustrating various X groups (I through VIII) for forming the stabilizing agents disclosed in the present invention.

FIG. 3 is a chart illustrating various RX compounds evaluated as stabilizing agents disclosed in the present invention. "Working conc V/V %" refers to the concentration of the stabilizing agent tested that was soluble.

FIG. 4 is a chart illustrating various EHS homologs evaluated as stabilizing agents disclosed in the present invention. "Working cone V/V %" refers to the concentration of the stabilizing agent tested that was soluble.

DETAILED DESCRIPTION OF THE INVENTION

The present invention is directed to a composition for use in an assay measuring the concentration of a free analyte, the composition comprising a capture ligand for the free analyte and a stabilizing agent, with the proviso that the stabilizing agent does not comprise an alkyl amine fluoro-surfactant.

It is understood that as used in this specification and the appended claims, the singular forms "a," "an," and "the" include singular and plural references unless the context clearly dictates otherwise. Thus, for example, "a stabilizing agent" includes a single stabilizing agent as well as two or more different stabilizing agents in combination.

The term "optionally derivatized" refers to the subject molecule or molecular moiety being optionally substituted, optionally interrupted, or both. The term "optionally substituted" refers to the replacement of a hydrogen or carbon atom in a subject molecule or molecular moiety in exchange for an atom or group of atoms. The term "optionally interrupted" as described herein refers to the insertion of Si, O, N, S, or P into a backbone of a carbon chain or a siloxane chain. In some embodiments, the term "optionally derivatized" refers to the substitution or interruption with one or more oxygen, nitrogen, halogen, or a moiety containing an oxygen, nitrogen, or halogen.

The composition of the present invention can be used in an assay measuring the concentration of a free analyte. The composition can comprise (i) a capture ligand for the free analyte; and (ii) a stabilizing agent, wherein the stabilizing agent comprises the general formula RX, or salt thereof, wherein R is a saturated or unsaturated alkyl, aryl, or silicon-based polymer, any of which is optionally derivatized with one or more moiety containing oxygen, nitrogen, halogen, or combination thereof, and wherein X is an oxoanion or oxide of sulfur or phosphorus, an oxoanion or carbonyl derivative of nitrogen, a carboxylate, a borate, a silicate, or a halogen, with the proviso that the stabilizing agent does not comprise an alkyl amine fluoro-surfactant.

In some embodiments, the stabilizing agent comprises the general formula RX, or salt thereof, wherein R is a saturated or unsaturated alkyl, alkoxy, alkoxyalkyl, alkoxyalkoxyalkyl, alkylaminoalkyl, alkylaminooxyalkyl, alkoxyaminoalkyl, phosphonoalkyl, carboxyalkyl, carboxyalkoxyalkyl, carboxyalkylaminoalkyl, carboxyalkylamidoalkyl, cycloalkyl, cycloalkylalkyl, heterocycloalkylalkyl, heterocyclyl, aryl, arylalkyl, heteroaryl, heteroarylalkyl, siloxane, silicone, or carbosilane, any of which can be optionally interrupted with one or more oxygen, nitrogen, phosphorous, or silicon atoms, and wherein any one of the R substitutents can be optionally substituted with one or more hydroxy, carbonyl, halogen, phosphate, acetyl, ammonium, or combinations thereof, and wherein X is sulfate, sulfonic acid, sulfonate, sulfite, taurate, sulfosuccinate, sulfobetaine, sulfonamide, methoxymethanilamide, sulfamyl, sulfeno, chlorite, chloride, iodide, iodate, bromide, bromate, fluoride, fluorate, nitrate, nitrite, nitroamine, amino, imino, isocyanoto, isothiocyano, acetamido, acetimido, azido, diazo, cyano, cyanato, phosphate, phospho, phosphono, phosphinyl, phosphino, carboxylate, acrylate, sebacate, phthalate, acetate, oxide, borate, peroxoborate, tetraborate, boranate, silane, orthosilcate, metasilicate, or a metal silicate with the proviso that RX is not an alkyl amine fluoro-surfactant, i.e., R is not a fluoro alkyl amine.

FIGS. 1 and 2 outline various R and X groups of the stabilizing agent of the present invention. In some embodiments, the stabilizing agents may be of a formula RX. In other embodiments, the stabilizing agents may be of a formula such as RXR', XRX' and RXR'X'. In the present invention, when the stabilizing agent is of the formula RXR', XRX' and RXR'X', then R and R', or X and X', can be the same subject molecule or molecular moiety, or optionally they can be different subject molecules or molecular moieties.

In some embodiments, R is selected from the group consisting of straight or branched siloxane, straight or branched carbosilane, straight or branched alkyl, cycloalkyl, heterocyclyl, arylalkyl, heteroaryl, and combinations thereof. In some embodiments, R is an alkyl, aryl, or silicon-based polymer optionally substituted with one or more hydroxy, keto, carbonyl, carboxy, or combinations thereof. In some embodiments, R is an ether, an ester, or combination thereof. In some embodiments, R comprises polyoxypropylene or polyoxyethylene.

In some embodiments, R is an alkyl, aryl, or silicon-based polymer optionally substituted with one or more nitrogen-containing moiety comprising amine, amino, imine, imino, amide, ammonium, or combination thereof.

In some embodiments, R can be alkyl, alkylene, alkyne, alkoxyalkyl, alkoxyalkoxyalkyl, alkylaminoalkyl, alkylaminooxyalkyl, alkoxyaminoalkyl, phosphonoalkyl, carboxyalkyl, carboxyalkoxyalkyl, wherein any one of which is optionally substituted with one or more hydroxy, carbonyl, halogen, phosphate, acetyl, ammonium, or combinations thereof.

In some embodiments, R as defined herein can be optionally substituted with hydroxy, carboxy, amine, amine oxide, phosphate, acetate, carboxylate, ammonium derivatives of alkyl or aryl, or combinations thereof. In some embodiments, R is optionally substituted with one or more hydroxy, oxo, acetate, ammonium, carboxy, amino, or amine oxide.

In some embodiments, R is alkyl or aryl, wherein any one of which is optionally substituted with one or more hydroxy, carbonyl, halogen, phosphate, acetyl, ammonium, or combinations thereof. Embodiments of the invention include wherein R is alkyl, and alkyl is a $C_{1-30}$ alkyl, $C_{1-22}$ alkyl, $C_{1-16}$ alkyl, $C_{1-12}$ alkyl, $C_{1-10}$ alkyl, or $C_{1-8}$ alkyl. In some embodiments, the alkyl moiety is $C_{4-30}$ alkyl, $C_{4-22}$ alkyl, $C_{4-18}$ alkyl, $C_{4-16}$ alkyl, $C_{4-14}$ alkyl, or $C_{4-12}$ alkyl. In some embodiments, the alkyl moiety is $C_{6-30}$ alkyl, $C_{6-22}$ alkyl, $C_{6-18}$ alkyl, $C_{6-16}$ alkyl, $C_{6-14}$ alkyl, or $C_{6-12}$ alkyl. In some embodiments, the alkyl is a $C_{7-30}$ alkyl, $C_{7-22}$ alkyl, $C_{7-18}$ alkyl, $C_{7-14}$ alkyl, $C_{7-12}$ alkyl, or $C_{7-9}$ alkyl, optionally substituted with one or more hydroxy, carbonyl, halogen, phosphate, acetyl, ammonium, or combinations thereof.

Alkyl substituents can include ethyl, propyl, isopropyl, butyl, isobutyl, pentyl, hexyl, heptyl, octyl, 2-methyl butyl, 2-ethyl butyl, 2-propyl butyl, 3-methyl butyl, 3-ethyl butyl, 3-propyl pentyl, 2-methyl pentyl, 2-ethyl pentyl, 2-propyl pentyl, 3-methyl pentyl, 3-ethyl pentyl, 3-propyl pentyl, 4-methyl pentyl, 4-ethyl pentyl, 4-propyl pentyl, 2-methyl hexyl, 2-ethyl hexyl, 2-propyl hexyl, 3-methyl hexyl, 3-ethyl hexyl, 3-propyl hexyl, 4-methyl hexyl, 4-ethyl hexyl, 4-propyl hexyl, 5-methyl hexyl, 5-ethyl hexyl, 5-propyl hexyl, 2-methyl heptyl, 2-ethyl heptyl, 2-propyl heptyl, 3-methyl heptyl, 3-ethyl heptyl, 3-propyl heptyl, 4-methyl heptyl, 4-ethyl heptyl, 4-propyl heptyl, 5-methyl heptyl, 5-ethyl heptyl, 5-propyl heptyl, 6-methyl heptyl, 6-ethyl heptyl, 6-propyl heptyl, 2-methyl octyl, 2-ethyl octyl, 2-propyl octyl, 3-methyl octyl, 3-ethyl octyl, 3-propyl octyl, 4-methyl octyl, 4-ethyl octyl, 4-propyl octyl, 5-methyl octyl, 5-ethyl octyl, 5-propyl octyl, 6-methyl octyl, 6-ethyl octyl, and 6-propyl octyl, any of which can be optionally substituted with one or more hydroxy, carbonyl, halogen, phosphate, acetyl, ammonium, or combinations thereof.

In some embodiments, R can be an olefin homolog of alkyl, with one or more unsaturated carbon to carbon bond(s). That is, in some embodiments, any one of the substituents of R as described herein can be unsaturated. Examples of unsaturated substituents for R include, but are not limited to, alkenyl, alkenoxy, alkenyloxyalkyl, alkenyloxyalkoxyalkyl, alkenylaminoalkyl, alkenylaminooxyalkyl, alkenyloxyaminoalkyl, phosphonoalkenyl, carboxyalkenyl, carboxyalkenyloxyalkyl, carboxyalkenylaminoalkyl, carboxyalkenylamidoalkyl. The term "alkenyl" refers to $C_{2-22}$ alkenyl groups, preferably $C_{4-18}$ alkenyl, or more preferably $C_{6-18}$ alkenyl or $C_{7-14}$ alkenyl. The term alkenyl includes all stereoisomers, i.e., cis and trans isomers, as well as the E and Z isomers. In some embodiments, the unsaturated alkyl can comprise an alkyne. The term "alkyne" refers to $C_{2-22}$ alkyne groups, preferably $C_{4-18}$ alkyne, or more preferably $C_{6-18}$ alkyne or $C_{7-14}$ alkyne, wherein one or more triple bonds can exist in the alkyl chain.

In some embodiments, any one of the substituents as defined herein for R can be saturated.

In some embodiments, R can be a cyclic, polycyclic, or heterocyclic derivative of alkyl or aryl, i.e., R is a cycloalkyl, heterocyclyl, aryl, or heteroaryl. In some embodiments, the cycloalkyl, heterocyclyl, aryl or heteroaryl can be optionally substituted with one or more hydroxy, carbonyl, halogen, phosphate, acetyl, ammonium, or combinations thereof. In some embodiments, the term cycloalkyl, heterocyclyl, aryl or heteroaryl can refer to a bicyclic ring, or a tricyclic ring.

The term "cycloalkyl" refers to a cyclized alkyl group that is saturated or partially unsaturated. Cycloalkyl groups can include $C_{3-8}$ cycloalkyl. Typical cycloalkyl groups include cyclopropyl, cyclobutyl, cyclopentyl, cyclohexyl and cycloheptyl.

The term "heterocyclyl" or "heterocyclic" refers to a derivative of cycloalkyl interrupted with Si, O, N, P, or combinations thereof. More specifically, the term "heterocyclyl" or "heterocyclic" is used herein to refer to a saturated or partially unsaturated 3-7 membered monocyclic, or 3-14 membered bicyclic, ring system that consists of carbon atoms and from one to four heteroatoms independently selected from the group consisting of Si, O, N, P, or combinations thereof. Examples include, but are not limited to, tetrahydrofuranyl, tetrahydropyranyl, pyrrolidinyl, piperidinyl, piperazinyl, pyrazolidinyl, dihydrofuranyl, morpholinyl, dihydroimidazolyl, dihydropyranyl, dihydrooxazolyl, tetrahydrooxazolyl, 2-azabicyclo[2.2.1]heptanyl, 2,5-diazabicyclo[2.2.1]heptanyl, oxazinyl, isoxazinyl, oxathiazinyl, and the like. Heterocyclic groups can be optionally substituted with one or more methyl, ethyl, oxo, halo, hydroxy, amino, alkylamino, hydroxymethyl, hydroxyethyl, hydroxypropyl, methoxymethyl, carboxy, or combinations thereof. In some embodiments, the term "heterocyclyl" refers to a cycloalkyl group that contains oxygen in the ring, i.e., a cyclic ether such as tetrahydropyran or tetrahydropyran. In some embodiments, the term "heterocyclyl" refers to a cycloalkyl group that contains nitrogen and oxygen in the ring.

The term "aryl" refers to any aromatic carbon ring structure, or any carbon ring structure with aromatic properties. Preferred aryls include $C_{6-14}$ aryl, especially $C_{6-10}$ aryl, such as phenyl or naphthyl, and most preferably six carbon aryl. Aryl groups are optionally substituted with one or more methyl, ethyl, hydroxy, alkoxy, amino, alkylamino, halo, hydroxymethyl, hydroxyethyl, hydroxypropyl, methoxymethyl, or carboxy. Preferably aryl groups are optionally substituted with one or more methyl, ethyl, halo, hydroxymethyl, hydroxyethyl, or carboxy.

The term "heteroaryl" refers to a derivative of aryl, wherein the aryl ring is interrupted with one or more Si, O, N, P, or combinations thereof. More specifically, the term "heteroaryl" refers to 5-14 membered heteroaromatic ring systems and most preferably to five or six membered heteroaromatic ring systems, wherein from one to four atoms in the ring structure are heteroatoms independently selected from the group consisting of Si, O, N, P, or combinations thereof. Examples include, but are not limited to, tetrazolyl, pyridinyl, imidazolyl, isoxazolyl, furanyl, oxazolyl, thiazolyl, pyrrolyl, thienyl, pyrazolyl, triazolyl, e.g., 1,2,3-triazolyl and 1,2,4-triazolyl, isothiazolyl, oxadiazolyl, e.g., 1,2,3-oxadiazolyl, 1,2,4-oxadiazolyl, 1,2,5-oxadiazolyl, and 1,3,4-oxadiazolyl, oxatriazolyl, pyridazinyl, pyrimidinyl, pyrazinyl, triazinyl, e.g., 1,2,3-triazinyl and 1,2,4-triazinyl, quinolinyl, isoquinolinyl, indolyl, benzofuranyl, benzothienyl, benzimidazolyl, and indazolyl. In some embodiments, the term "heteroaryl" refers to an aryl group that contains oxygen, nitrogen, or both in the ring.

In some embodiments, R is a fatty acid, or a homolog of a fatty acid. The term fatty acid refers to a saturated or unsaturated carboxyalkyl, carboxyalkoxyalkyl, carboxyalkylaminoalkyl, carboxyalkylamidoalkyl, or salt or ester thereof, optionally substituted with hydroxy, $C_{1-4}$ alkyl, halo, or alkoxy. In some embodiments, the carboxyalkyl is a saturated or unsaturated $C_{2-30}$ carboxyalkyl, $C_{2-20}$ carboxyalkyl, $C_{2-18}$ carboxyalkyl, $C_{2-16}$ carboxyalkyl, $C_{2-14}$ carboxyalkyl, $C_{2-10}$ carboxyalkyl, or $C_{2-8}$ carboxyalkyl, optionally interrupted with one or more Si, O, N, P, or combinations thereof. In some embodiments, the term carboxyalkyl is a $C_{6-30}$ carboxyalkyl, $C_{6-20}$ carboxyalkyl, $C_{6-18}$ carboxyalkyl, $C_{6-16}$ carboxyalkyl, $C_{6-14}$ carboxyalkyl, $C_{6-10}$ carboxyalkyl, or $C_{6-8}$ carboxyalkyl, optionally substituted with one or more Si, O, N, P, or combinations thereof. In some embodiments, the carboxyalkyl is butanoic acid, hexanoic acid, octanoic acid, decanoic acid, dodecanoic acid, tetradecanoic acid, hexadecanoic acid, octadecanoic acid, icosanoic acid, or docosanoic acid.

In some embodiments, R is an ester of a fatty acid, i.e., R is a carboxyalkyl optionally interrupted with an ester. Examples of carboxyalkyls interrupted with an ester include, but are not limited to, carboxyalkoxyalkyl or carboxyalkoxyalkoxyalkyl. In some embodiments, R is an alkanoamide derivative of a fatty acid, i.e., R is a carboxyalkyl interrupted with an amido group. For example, in some embodiments R is a carboxyalkylamido or carboxyalkylamidoalkyl. In some embodiments, R is an oxyethylated fatty acid.

In the present invention, R can be a derivative of fatty acid optionally interrupted with Si, O, N, P, or combinations thereof, i.e., in some embodiments, R is a carboxyalkyl optionally interrupted with Si, O, N, P, or combinations thereof. In some embodiments, R is a carboxyalkyl optionally substituted with a halogen. In some embodiments, R is a charged carboxyalkyl, i.e., R is an anionic or cationic derivative of a fatty acid.

In some embodiments, R is an alcohol or alcohol derivative. For example, R can be an alkylphenol, or an ester of an alcohol. In some embodiments, R is an alcohol or phenol optionally interrupted with Si, O, N, P, or combinations thereof, optionally substituted with a halogen, or both.

In some embodiments, R is an ester or polyester derivative of an alkyl. For example, in some embodiments, the R is a saturated or unsaturated alkoxyalkyl, alkoxyalkoxyalkyl, or alkoxyalkoxyalkoxyalkyl, preferably $C_{2-20}$ alkoxyalkyl, $C_{2-20}$ alkoxyalkoxyalkyl, or $C_{2-20}$ alkoxyalkoxyalkoxyalkyl; a $C_{5-16}$ alkyl, $C_{5-16}$ alkoxyalkyl, $C_{5-16}$ alkoxyalkoxyalkyl, $C_{5-16}$ alkoxyalkoxyalkoxyalkyl; or a $C_{7-14}$ alkoxyalkyl, $C_{7-14}$ alkoxyalkoxyalkyl, or $C_{7-14}$ alkoxyalkoxyalkoxyalkyl; any one of which can be optionally substituted with one or more hydroxy. In some embodiments, the term polyester is a compound of the general formula $[(CH_q)_nCO_2X_p]_m$, wherein X is $C_{1-10}$ alkyl, $C_{1-10}$ alkenyl, or $C_{1-10}$ alkoxyalkyl, p is 0 or 1, q is 1 or 2, n is 1-10, and m is 1-100, preferably 1-20 or 1-10. In some embodiments, the ester or polyester derivative of alkyl is optionally substituted with one or more hydroxy.

In some embodiments, R is a polyoxyalkylene. The term polyoxyalkylene refers to an alkylene subject molecule or molecular moiety interrupted with two or more oxygen atoms. In some embodiments, the term polyoxyalkylene refers to a $C_{1-21}$, $O_{1-14}$ polyoxyalkylene, or a $C_{1-14}$, $O_{1-7}$ polyoxyalkylene. Examples of polyoxyalkylenes suitable for use in the present invention include, but are not limited to, polyoxyethylene, polyoxypropylene, polyoxybutylene, polyoxypentylene, polyoxyhexylene, polyoxyheptylene, or polyoxyoctylene. In some embodiments, an R is a copolymer of two or more polyoxyethylene, polyoxypropylene, polyoxybutylene, polyoxypentylene, polyoxyhexylene, polyoxyheptylene, or polyoxyoctylene groups. In some embodiments, R is an oxyethylated copolymer with other organic or inorganic moieties.

In some embodiments, R can be a polyamine, amine oxides, amine ethoxylates and other amine derivatives of alkyl. The term "polyamine derivative" refers to an alkyl chain wherein two or more carbon atoms in the alkyl chain are replaced with nitrogen. The term also includes monoalkyl amines as well as dialkyl amines. The term "amine oxide derivative" refers to an alkyl chain wherein two or more carbon atoms in the alkyl chain have been replaced with a nitrogen and an oxygen (i.e., —N—O—). For example, R can be alkylaminooxyalkyl, carboxyalkylaminooxyalkyl, alkylaminooxyalkyl, or alkoxyaminoalkyl. In some embodiments, the polyamine derivative or amine oxide derivative is optionally substituted with an ethyoxylate.

In some embodiments, R is a silicon-based polymer. The term "silicon-based polymer" refers to linked monomers, each monomer containing at least one silicon atom. For example, the term silicon-based polymer can include, but is not limited to, siloxanes, silicones, or carbosilanes. In some embodiments, the silicon-based polymer can be end-blocked with a non-silicon containing end group.

In some embodiments, R is a straight, branched, or cyclic siloxane. In some embodiments, R is a siloxane optionally substituted with one or more hydroxy, carbonyl, alkyl, halogen, haloalkyl, hydroxyalkyl, phosphate, acetyl, ammonium, or combinations thereof. In some embodiments, R is a $Si_{1-21}$, $O_{1-21}$ siloxane, a $Si_{3-14}$, $O_{3-14}$ siloxane, or a $Si_{5-10}$, $O_{5-10}$ siloxane. In other embodiments, R is a carbosilane. The term carbosilane refers to a polymer with carbon and silicon in its backbone. In some embodiments, R is a carbosilane optionally substituted with one or more hydroxy, carbonyl, alkyl, halogen, haloalkyl, hydroxyalkyl, phosphate, acetyl, ammonium, or combinations thereof. In some embodiments, R is a $Si_{1-21}$, $C_{1-21}$ carbosilane, a $Si_{3-14}$, $C_{1-14}$ carbosilane, or a $Si_{5-10}$, $C_{5-10}$ carbosilane. In some embodiments, the siloxane or carbosilane is end-blocked, e.g., end-blocked with vinyl or silanone. In some embodiments, R is a siloxane or carbosilane optionally substituted with one or more alkyl, halogen, haloalkyl, hydroxyalkyl, or combinations thereof. For example, in some embodiments, the siloxane or carbosilane can be methyl, ethyl, propyl, butyl, or pentyl substituted, or combinations thereof.

In some embodiments, R comprises copolymers of silicone with polyether, polyester, polyol, polyamine, polyurethane, polyoxyethylene, polyoxypropylene, and other polymeric moieties. For example, in some embodiments, R is a siloxane or carbosilane optionally substituted with one or more polyester, polyol, polyamine, polyurethane, polyoxyethylene, polyoxypropylene, or combination thereof. The siloxane or carbosilane of the present invention can include their salts, ethers, and esters. In some embodiments, R is a charged siloxane or carbosilane, e.g., a cationic derivative or anionic derivative of a siloxane. In some embodiments, R is a salt of a siloxane or carbosilane, e.g., an ammonium salt. In some embodiments, R comprises silicones derivatized with long chain ester, long chain alcohol, long chain amine, or combinations thereof.

Various X functional groups can be provided by the present invention. In some embodiments, X is an oxoanion or oxide of sulfur or phosphorus, an oxoanion or carbonyl derivative of nitrogen, a carboxylate, a borate, or a silicate. In some embodiments, X is sulfate, sulfonic acid, sulfonate, sulfite, sulfoxide, taurate, sulfosuccinate, sulfobetaine, sulfatobetaine, sulfonamide, phosphate, phospho, phosphono, phosphinyl, nitrate, nitrite, amino, imino, isocyano, isothiocyano, acetamido, acetimido, azido, diazo, cyano, cyanato, alkylcarboxylate, acrylate, sebacate, phthalate, borate, tetraborate, orthosilicate, metasilicate, metal silicate, chlorite, chloride, iodide, iodate, bromide, bromate, fluoride, or fluorate. In some embodiments, X is sulfate, sulfonic acid, sulfonate, sulfosuccinate, or taurate.

In some embodiments, X is a functional group that contains a sulfur atom. Examples include, but are not limited to any functional group that contains sulfate, sulfonate or sulfonic acid. The term "oxoanion or oxide of sufur" refers to a sulfate, sulfonic acid, sulfonate, sulfite, taurate, sulfosuccinate, sulfobetaine, sulfonamide, methoxymethanilamide, sulfamyl, or sulfeno.

In some embodiments of the present invention, X can be any functional group that contains a halogen. Examples include, but are not limited to, any functional group that contains a chloro, fluoro, bromo, iodo group, or combinations thereof. In some embodiments, X can be chlorite, chloride, iodide, iodate, bromide, bromate, fluoride or fluorate.

In some embodiments of the present invention, X can be any functional group that contains a nitrogen. Examples include, but are not limited to, any functional group that contains a nitrate, nitrite, nitroamine, amino, imino, isocyanoto, isothiocyano, acetamido, acetimido, azido, diazo, cyano, cyanato, nitroso, nitrosoimino, nitramino, nitro, or combinations thereof.

In some embodiments, X can be any functional group that contains a phosphorus. The term "oxoanion or oxide of phosphorous" refers to a phosphate, phospho, phosphono, phosphinyl, or phosphino.

In some embodiments, X is carboxylate, acrylate, sebacate, phthalate, acetate, or oxide. In some embodiments, X can be any functional group that contains a boron. Examples include, but are not limited to borate, peroxoborate, tetraborate, or boranate.

In the present invention, X can be any functional group that contains a silicon atom. Examples include, but are not limited to, silane, orthosilcate, metasilicate, or a metal silicate.

Many stabilizing agents were screened to determine which, if any, could replace the alkyl amine fluoro-surfactant and yet have no negative impact on the accuracy of the assays. Without being limited by theory, we postulate that the stabilizing agents maintain a sample's ratio between free analyte and bound analyte thereby preventing the disruption of the free unbound analyte versus bound analyte equilibrium found in the biological fluid of a subject or in an in vitro system.

In one embodiment, the stabilizing agent comprises the general formula RX, wherein R comprises a chemical group containing an alkyl, an aryl, a fatty acid, an alcohol, an ester, an ether, an oxyalkylate, or a siloxane, and X comprises a chemical group containing sulfur. When RX comprises a halogen, the halogen moiety may be any halogen, e.g., F, Cl, Br, or I, with the proviso that the present invention does not comprise an alkyl amine fluoro-surfactant, such as FC100.

In one embodiment, the present invention identifies the stabilizing agent as an alkyl alcohol derivative compound, for example 2-ethyl-hexyl sulfate (EHS). The general chemical structure of such alkyl alcohol derivative compounds is $C_nH_{2n+1}X$ wherein n is about 6 to about 18 and X is a sulfate derivative, for example $SO_4^-Na^+$ for 2-ethyl-hexyl sulfate sodium salt having the chemical structure: $CH_3(CH_2)_3CH(C_2H_5)CH_2OSO_3^-Na^+$. X may also be any of the sulfur-containing groups disclosed in FIG. 2, Group X.

Other stabilizing agents suitable for use in the present invention include: 1-hexane sulfonic acid, or salt thereof (for example, Na+ salt); 1-heptane sulfonic acid, or salt thereof (for example, Na+ salt); 1-octane sulfonic acid, or salt thereof (for example, Na+ salt); 1-decane sulfonic acid, or salt thereof (for example, Na+ salt); sodium $C_{14-16}$ olefin sulfonate (CAS#68439-57-6); sodium dodecyl sulfate; sodium dioctyl sulfosuccinate; sodium N-oleyl-N-methyltaurate; sodium polyoxyethylene lauryl sulfate (molecular weight: 346); amine alkylbenzyl sulfonate (molecular weight: 385); and sodium ethyl-hexyl sulfate.

The present invention provides new and useful compositions for use in the diagnostic measurement of free or unbound analyte concentrations in a fluid. In some embodiments, the analyte is present in a biological fluid. The biological fluid may be plasma or serum. It may also be comprised of seminal fluid, saliva, urine, fecal solutions, cerebral spinal fluid, or gastric fluids. Generally, however, the biological fluid is plasma or serum. The compositions of the present invention may also be used in an in vitro system comprising cell culture supernate or filtrate. The term "biological fluid" includes fluids from a biological organism, as well as fluids derived from a biological organism, e.g., fluids that have been fractionated, diluted, chemically modified, or combinations thereof.

The analyte may be any small molecule such as, but not limited to, a hormone, a drug, or a vitamin. In some embodiments, the analyte is present in an equilibrium state between the free unbound condition and the bound condition (e.g. protein bound). For example, the analyte can be a thyroid hormone or vitamin B12. Other analytes suitable for use in the present invention include the following classes of vertebrate hormones:

Amine Hormones:
    a. Tyrosine-derived (Simple aromatic rings)
        Catecholamines (e.g. adrenaline, noradrenaline, dopamine).
        Thyroid hormones (e.g. T4, or isomers of T3, T2, and T1).
    b. Tryptophan-derived (Polycyclic and heterocyclic aromatic compounds)
        Melatonin, serotonin.

Peptide Hormones:
  a. Small peptides, e.g.
    Angiotensin IV has 6 amino acid residues, Angiotensin III & Angiotensin II have 7 & 8 amino acids, respectively. Due to the small molecular size, these peptides are likely bound to plasma carrier molecules, such as proteins.
    Brain natriuretic peptide (BNP), 32 amino acids. Other natriuretic peptide hormones include atrial natriuretic peptide (ANP) and C-type natriuretic peptide (CNP).
    Calcitonin, 32 amino acids peptide, derived from the precursor, procalcitonin.
    Adrenocorticotropic hormone (ACTH) has 39 amino acids.
    Insulin is a 51 amino acids peptide.
    Parathyroid hormone (PTH), 84 amino acids. PTH can also occur in several different fragments having different clinical utilities: intact PTH; N-terminal PTH; mid-molecule PTH, and C-terminal PTH.
  b. Large peptides (large peptides yield smaller protein molecules after dissociation of protein multimers or after fragmentation. These smaller molecules may circulate in an equilibrium with carrier molecules), e.g.:
    Follicle-stimulating hormone (FSH).
    Luteinizing hormone (LH).
    Thyroid-stimulating hormone (TSH).
    Chorionic gonadotropin (e.g. hCG).
    Thyrotropin-releasing hormone (TRH).
    Prolactin (PRL).
    Erythropoietin (EPO).
Steroid or Sterol Hormones: This invention is useful for those steroid or sterol hormones that have a free form in equilibrium with a form that is bound to plasma transport molecules, such as proteins. The free form is biologically active and has clinical utility.
  a. Steroid hormones, e.g:
    Cortisol: About 4% of circulating cortisol is free and therefore available to receptors. The remainder is bound to proteins including corticosteroid binding globulin (CBG) and albumin.
    Testosterone: About 2-3% of the circulating testosterone is free; the remainder is bound to testosterone binding proteins including sex hormone binding globulin (SHBG, about 44%) and cortisol binding globulin (CBG, about 3.5%), as well as to albumin (about 50%).
    Dehydroepiandrosterone (DHEA). A small percentage of DHEA occurs as a free form, although the majority is strongly bound to sex steroid binding globulin and weakly bound to corticosteroid binding globulin and albumin.
    Progesterone: A small percentage of progesterone occurs as a free form, although the majority is bound to cortisol binding globulin and albumin.
    Estriol: Estriol occurs as a free form or bound to sex hormone binding globulins.
    Estradiol: About 1-3% of the circulating hormone is free while the remainder is strongly bound to estrogen binding globulin.
  b. Sterol hormones:
    Vitamin D derivatives.
    Calcitriol.
The term thyroid hormone refers to thyroxine (T4), triiodothyronine (T3), diiodothyronine (T2), monoiodothyronine (T1), and combinations thereof. It is understood that the thyroid hormones can be comprised of their salts, their L- or D-enantiomers, or their de-iodinated and isomeric forms.

For purposes of the present invention, it is understood that the term "analyte" encompasses all enantiomers and isomers of that particular analyte, either in a mixture or a homogenous environment. For analytes in a biological fluid, the analyte can originate either exogenously or endogenously. In some embodiments, the analyte can be in a biological fluid from a primate such as apes, monkeys, orangutans, baboons, gibbons, and chimpanzees; canids such as dogs and wolves; fields such as cats, lions, and tigers; equids such as horses, donkeys, and zebras, food animals such as cows, pigs, and sheep; and rabbits, mice, rats, guinea pigs, and ferrets. The analyte can also be in a fluid from a model animal, e.g., disease model animal such as mice, rats, or other laboratory animal; an economically valuable animal, e.g., economically important breeding stock, racing animals, show animals, heirloom animals, rare or endangered animals, or companion animals. In particular, the analyte is in a biological fluid from a human. The term "subject," as used herein, refers to any mammal, including humans and non-humans, such as, but not limited to, domestic and farm animals, zoo animals, sports animals, and pets.

The stabilizing agent may be incorporated into a reagent buffer, or a wash buffer, or both. It can also be mixed with a capture ligand. Under other embodiments, it can be a separate solution.

In one embodiment, the present invention is directed to a composition for use in an assay measuring the concentration of an analyte, in some embodiments a free analyte, the composition comprising a capture ligand and a stabilizing agent.

Capture ligands are analyte-specific and may comprise any substance capable of selectively binding the free analyte of interest. Examples of capture ligands include, but are not limited to, antibody, antibody fragment, antibody mimic, or analyte-specific binding protein such as intrinsic factor or folate-binding protein, and combinations thereof.

As used herein, the term "antibody" is intended to include all forms such as, but not limited to, polyclonal, monoclonal, purified IgG, purified IgM, purified IgA, or combinations thereof; single chain antibodies (U.S. Pat. No. 4,946,778), chimeric or humanized antibodies (Morrison et al., 1984, Proc. Nat'l Acad. Sci. USA 81:6851; Neuberger et al., 1984, Nature 81:6851) and complementary determining regions (CDR; see Verhoeyen and Windust, in Molecular Immunology 2ed., by B. D. Hames and D. M. Glover, IRL Press, Oxford University Press, 1996, at pp. 283-325). The term "antibody fragment" includes, but is not limited to, fragments such as Fv, single chain Fv (scFv), F(ab')$_2$, and Fab fragments (Harlow and Leon, 1988, Antibody, Cold Spring Harbor). Antibodies and antibody fragments of the present invention can be obtained by any conventional methods, such as, but not limited to, the methods described in *Antibodies: A Laboratory Manual* (E. Harlow, D. Lane, Cold Spring Harbor Laboratory Press, 1989) that is incorporated herein by reference in its entirety.

The term "antibody mimic" refers to chemicals that mimic the functions of antibodies. Antibody mimics are generally small in size, allowing them to avoid provoking an immunogenic response. There are several approaches to the structure and manufacture of these antibody mimics, such as alternative protein frameworks; structures comprising RNA; unnatural oligomers such as benzodiazepines, beta-turn mimics, protease inhibitors and purine derivatives; unnatural biopolymers such as oligocarbamates, oligoureas and oligosulfones; and the joining of various substituents to scaffolds such as xanthene and cubane as described in Hsieh-Wilson, et al., (1996) *Acc. Chem Res.* 29:164-170, and U.S. Pat. No. 5,770,380.

The term "intrinsic factor" refers to a glycoprotein necessary for the absorption of vitamin $B_{12}$. In some embodiments, the term "instrinsic factor" refers to human intrinsic factor.

The term "analyte-specific binding protein" can include any non-antibody protein that binds specifically to an analyte. Examples of analytes with their analyte-specific binding proteins include, but are not limited to: thyroxine/thyroxine-binding globulin; enzyme inhibitor, coenzyme or cofactor/enzyme; cortisol/cortisol binding protein; vitamin B12/intrinsic factor; and folate/folate-binding protein. In some embodiments, the analyte-specific binding protein is the capture ligand. In some embodiments, the analyte-specific binding protein is folate-binding protein or intrinsic factor.

In one embodiment, the composition of the present invention can comprise a capture ligand, a stabilizing agent, and can further comprise salts, such as ammonium salts, sodium salts, potassium salts, calcium salts, magnesium salts, zinc salts, chloride salts, carboxylate salts, phosphate salts, inorganic sulfate salts, or combinations thereof.

In one embodiment, the present invention is directed to a composition for use in an assay measuring the concentration of an analyte. In some embodiments, the analyte exists as a free analyte and a bound analyte, and the invention is directed to an assay measuring the concentration of the free analyte. The term "free analyte" refers to an analyte that is not bound, either specifically or nonspecifically, to other molecular species such as proteins, other than a capture ligand. Thus, the free analyte is not associated with other molecular species in the fluid. The term "bound analyte" refers to an analyte that is associated, either specifically or nonspecifically, with other molecular species such as proteins, other than a capture ligand. In some embodiments, to stabilize the ratio of free to bound analyte, the present invention employs one or more stabilizing agents comprising the general formula RX.

The stabilizing agent can be present in various concentrations. When describing the concentration of the stabilizing agent herein, the term "volume percent" refers to the volume of the stabilizing agent per unit volume of the final composition. The term "final composition" refers to the composition comprising the capture ligand and the stabilizing agent. Thus, e.g., if 1 ml of stabilizing agent was added to 49 ml of wash buffer, and the stabilizing agent/wash buffer was placed in 50 ml of a solution containing the analyte and the capture ligand, then the volume percent would be 1% of stabilizing agent (i.e., 1 ml stabilizing agent in 100 ml final composition). Suitable volume percents of a stabilizing agent in a final composition include, but are not limited to, about 0.00001 to about 0.5 volume percent, about 0.00005 to about 0.4 volume percent, about 0.00009 to about 0.3 volume percent, about 0.0001 to about 0.1 volume percent, about 0.0002 to about 0.2 volume percent, or about 0.00015 to about 0.15 volume percent, wherein the above volume percents are based on the total volume of a final composition. Since the binding affinity of an analyte for its analyte-specific binding protein determines the equilibrium between free analyte and bound analyte forms, one of skill in the art can optimize the percentage of stabilizing agent for a particular analyte on a case by case basis.

The concentration of the stabilizing agent can also be measured in moles of stabilizing agent per liter of the final composition. The concentration of a stabilizing agent in a final composition can be generally about 1 to about 900 micromolar, about 5 to about 850 micromolar, about 25 to about 800 micromolar, about 40 to about 800 micromolar, about 5 to about 750 micromolar, about 30 to about 700 micromolar, or about 25 to about 600 micromolar.

In embodiments wherein the stabilizing agent is EHS, the volume fraction of EHS in a final composition is generally about 0.0001 to about 0.05 volume percent, about 0.0005 to about 0.04, about 0.0009 to about 0.03, about 0.001 to about 0.02, about 0.002 to about 0.019, about 0.004 to about 0.015, or about 0.005 to about 0.01 volume percent, wherein the above volume percents are based on the total volume of a final composition.

In embodiments wherein the stabilizing agent is EHS, the concentration of EHS in a final composition can be generally about 50 to about 800 micromolar, about 100 to about 750 micromolar, about 150 to about 700 micromolar, about 150 to about 650 micromolar, about 200 to about 600 micromolar, about 250 to about 550 micromolar, or about 300 to about 500 micromolar.

With regard to the methods of the present invention, it is understood that the stabilizing agent can be present either upon mixing of the sample with the analyte-specific capture ligand or immediately thereafter. For example, the stabilizing agent can be added sequentially following the combination of the sample with the analyte-specific capture ligand as a component of a reagent buffer, a wash buffer, or both.

In certain embodiments, the present invention is also directed to a method for measuring a concentration of a free analyte, the method comprising:
 (a) adding a capture ligand for the free analyte to a vessel;
 (b) adding a stabilizing agent to the vessel;
 (c) adding a sample comprising the free analyte to the vessel;
 (d) adding a detection system to the vessel; and
 (e) measuring the concentration of the free analyte in the sample using the detection system.

It is recognized that the steps of the method for measuring a concentration of a free analyte can be performed in various sequential orders, with the proviso that step (e) must be the final step. Thus, e.g., step (b) can precede step (a), step (c) can precede step (b), or both, In some embodiments, the vessel may comprise a vial, a tube, a container for a reaction mixture, a microtiter plate well, a membrane in a lateral flow system, or other stable components of a liquid flow system.

The term "detection system" as used herein refers to one or more components of a system known to detect, either directly or indirectly, an analyte.

In some embodiments, the detection system comprises components of radioimmunoassays, enzyme-linked immunosorbent assays, enzyme immunoassays, chemiluminescent immunoassays, bioluminescent immunoassays, or fluorescent immunoassays. Such detection systems are well known in the literature. In some embodiments, the detection system comprises paramagnetic particles coated with a capture ligand-specific binding molecule, detectable label, or combination thereof. In some embodiments, the capture ligand-specific binding molecule is hapten-specific, and the capture ligand is haptenated. For example, in some embodiments the hapten is biotin. In some embodiments, the capture ligand-specific binding molecule is selected from the group consisting of streptavidin, avidin, biotin-specific antibody, biotin-specific antibody fragment, and biotin-specific antibody mimic.

In some embodiments, the detection system comprises a detectable label. As used herein, a "detectable label" has the ordinary meaning in the art and refers to an atom (e.g., radionuclide), molecule (e.g., fluorescein), or complex that is or can be used to detect (e.g., due to a physical or chemical property) or to indicate the presence of a molecule, or to reveal binding of another molecule to which it is covalently bound or with which it is otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, radiological, biochemical, immunochemical, electrical, optical or chemical means.

Labels useful in the present invention include fluorescent dyes (e.g., fluorescein, Texas red, rhodamine, green fluorescent protein, enhanced green fluorescent protein, lissamine, phycoerythrin, Cy2, Cy3, Cy3.5, Cy5, Cy5.5, Cy7, Fluor X, SyBR Green I & II [Molecular Probes], and the like), radiolabels (e.g., $^3H$, $^{125}I$, $^{35}S$, $^{14}C$ or $^{32}P$), enzymes (e.g., hydrolases, particularly phosphatases such as alkaline phosphatase, esterases and glycosidases, or oxidoreductases, particularly peroxidases such as horseradish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads. Techniques for detecting such labels are well known in the field.

Thus, for example, radiolabels may be detected using scintillation counters, chemiluminescent labels and fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the colored label.

Thus, a label is any composition detectable by spectroscopic, photochemical, radiological, biochemical, immunochemical, electrical, optical or chemical means. The label may be coupled directly or indirectly to the desired component of the assay according to methods well known in the art. Non-radioactive labels are often attached by indirect means. In some embodiments, a detectable label that is either inherently detectable or covalently bound to a signal generating system such as a detectable enzyme, fluorescent compound, or chemiluminescent compound (e.g., T4-ALP or T3-ALP in a competitive immunoassay for Free T4), competes with analyte (e.g., Free T4 in a fluid sample) for binding to a capture ligand (e.g., T4-specific monoclonal antibody). In some embodiments, the capture ligand may be directly immobilized on a solid phase. In some embodiments, the capture ligand may be biotinylated for indirect immobilization on a solid phase through its binding with a capture ligand-specific binding molecule such as streptavidin or biotin-specific monoclonal antibody.

Where an analyte has a natural, analyte-specific binding molecule, such an analyte can be detected or measured by using a labeled form either of the analyte or an analog of the analyte, or of the analyte-specific binding molecule in a detection system. In some embodiments, a capture ligand (e.g., Intrinsic Factor (IF)-specific monoclonal antibody) competes with analyte (e.g., vitamin B12) for binding to a natural, analyte-specific detectable label (e.g., IF-ALP in a competitive immunoassay for vitamin B12). In some embodiments, the capture ligand may be directly immobilized on a solid phase. In some embodiments, the capture ligand may be biotinylated for indirect immobilization on a solid phase through its binding with a capture ligand-specific binding molecule such as streptavidin or biotin-specific monoclonal antibody. The detectable label is either inherently detectable or covalently bound to a signal generating system such as a detectable enzyme, fluorescent compound, or chemiluminescent compound. Such detectable labels can be conjugated directly to signal generating compounds, e.g., by conjugation with an enzyme or fluorophore. Techniques for detecting labels are well known in the field and include, but are not limited to, use of a chemiluminescent agent, a colorimetric agent, an energy transfer agent, an enzyme, a substrate of an enzyme reaction, a fluorescent agent or a radioisotope. The enzyme may be selected from the group containing alkaline phosphatase, amylase, luciferase, catalase, beta-galactosidase, glucose oxidase, glucose-6-dehydrogenase, hexokinase, horseradish peroxidase, lactamase, urease and malate dehydrogenase. The substrate comprises those molecular groups upon which the preceding labels are known to act.

In some embodiments of the present invention the capture ligand is immobilized on a solid phase. A solid phase may be comprised of a protein coupling surface including, for example, a microtiter plate, a colloidal metal particle, an iron oxide particle, a polymeric bead, nanoparticles or microparticles. Further, the solid phase may be comprised of chemical or molecular aggregates that function as a solid phase in a separation system (e.g. fractionation, precipitation, or centrifugation).

In certain embodiments, the present invention is also directed to a kit for use in estimating a concentration of a free analyte, the kit comprising:
(a) a capture ligand for the free analyte;
(b) a stabilizing agent; and
(c) a detection system.

In some embodiments, the kit further comprises (d) a reference standard. Various reference standards can be used, depending on the analyte of interest. Generally, the reference standard comprises an analyte or its analog that has a known concentration and is used to estimate the concentration of the particular analyte to be measured. The reference standard can comprise a purified analyte, a recombinant, native or synthetic analyte, a drug, a hormone or a vitamin. The matrix portion of a reference standard matrix comprises a biological or synthetic fluid that can approximate the environment of the analyte in the sample to be measured.

In one particular embodiment, the present invention improves the accuracy of assays measuring concentrations of free non-protein bound thyroid hormones by using 2-ethylhexyl sulfate (EHS) and/or related compounds as a stabilizing agent. The present invention further improves diagnostic accuracy of measuring the bioavailable or free portion of thyroid hormones present in body fluid of a subject. The improvement in concentration accuracy measurements occurs by stabilizing the equilibrium of the free non-protein bound and protein-bound hormone inherent in a body fluid, such as serum or plasma.

In this embodiment, the present invention uses sulfonated or sulfated small molecules as the anionic salt component of the stabilizing agent. Traditionally, sulfates or sulfonates such as 8-anilino naphthalene-1-sulfonate (ANS) are used to displace protein bound analytes in order to measure total (bound plus free) hormone. Therefore, the inclusion of molecules with sulfonate or sulfate groups into the composition as stabilizing agents is expected to result in an artificial increase in the free-hormone fraction or an over-sampling diagnostic error. The present invention, therefore, is unexpected.

In this embodiment, surfactants or non-surfactants with sulfonate or sulfate groups improve the consistency of immunoassays by being added to the assay reaction as stabilizing agents. Without being limited by theory, it is postulated that the mechanism for enabling accurate concentration measurements of free thyroid hormones is by stabilization of the free to bound hormone equilibrium through the addition of EHS, or other small chain (6 to 18 carbons) anionic sulfates or sulfonates, early in the reaction. Among the various sulfated or sulfonated chemicals, those with sterically available sulfates or sulfonates act as suitable stabilizing agents. In some embodiments, other factors important for suitable stabilizing agents are described by a general formula RX, wherein R comprises a short chain hydrocarbon (that confers the hydrophobicity to one end of the molecule) and wherein X comprises a small hydrophilic group, e.g., a small chemical group containing more than one oxygen atom. FIGS. 1 and 2 illustrate, without intending to be limiting, some of the various R groups and X groups that can be combined to form a stabilizing agent of the present invention.

In one embodiment of the present invention, the analyte is a thyroid hormone. The following are points of interest to note regarding thyroid hormones.

1. Thyroxine (T4) is an essential hormone produced by the thyroid gland. Triiodothyronine (T3) can be directly released from thyroglobulin in the thyroid gland but most T3 is manufactured in other parts of the body by deiodination of thyroxine.
2. Via a reaction with the enzyme thyroperoxidase, iodine is covalently bound to tyrosine residues in thyroglobulin molecules, forming monoiodotyrosine (MIT) and diiodotyrosine (DIT). Thyroxine is produced by linking two moieties of DIT. Combining one molecule of MIT and one molecule of DIT produces triiodothyronine. MIT and DIT are formed in situ on thyroglobulin as inactive precursors of T4 and T3 hormones. Proteases in lysosomes digest iodinated thyroglobulin, releasing T3 and T4. MIT and DIT are also products of proteolysis, but they are degraded in situ by iodotyrosine dehalogenase.
3. Other constituents of the thyroid gland besides T4 and T3 include diiodothyronine (T2) and monoiodothyronine (T1).
4. Thyronamines are decarboxylated and deiodinated metabolites of the thyroid hormones thyroxine (T4) and 3,5,3'-triiodothyronine (T3).
5. The follicular cells in the thyroid gland synthesize the iodine-containing thyroid hormones, T4 and T3; the parafollicular cells of the thyroid gland produce calcitonin, a 32 amino acid peptide hormone cleaved from the larger polypeptide procalcitonin.

Thyroxine (T4), triiodothyronine (T3), diiodothyronine (T2), and monoiodothyronine (T1) in blood can be bound to serum proteins, and therefore only a fraction may be distributed in the free non-protein bound form, otherwise known as the bioavailable portion. This free amount is either increased or decreased in a thyroid disease state of a subject. For example, in hypothyroidism the free non-protein bound fraction in blood is decreased, whereas in hyperthyroidism the non-protein bound fraction is elevated.

The free thyroxine (FT4) test is used as a direct measurement of thyroid function and is commonly requested by physicians as a follow-up to, or in conjunction with, the thyroid stimulating hormone (TSH) test, in order to determine whether the thyroid status of a subject is euthyroid (healthy thyroid function), hypothyroid or hyperthyroid. However, it is more common to encounter misleading FT4 tests than misleading TSH measurements due to the binding-protein dependencies inherent with all free non-protein bound thyroid hormones and other interference factors that can alter the free to bound equilibrium. Therefore, it is important to include a stabilizing agent to stabilize FT4 when testing a sample from a subject for proper thyroid function.

In one embodiment of the present invention, the stabilizing agent is added to the assay before the sample containing the analyte is added. In other embodiments, the stabilizing agent can be added to the assay after the sample containing the analyte is added, e.g., as part of a reagent buffer. In some embodiments, the stabilizing agent is a part of a reagent kit containing a capture ligand (e.g., an analyte-specific antibody). In some embodiments, the stabilizing agent of the present invention can be added to an analyte-specific assay, e.g., FT4 assay, in various ways. For example, the stabilizing agent can be added by means of a vial system, a buffer system, or a pack system. In the vial system, the stabilizing agent, e.g., one or more sulfonated compounds, is added from vials to the reaction mixture. In the buffer system, the stabilizing agent, e.g., one or more sulfonated compounds, is part of a wash buffer solution which is added to the reaction mixture. In the pack system, the stabilizing agent, e.g., one or more sulfonated compounds, is taken from the well of the reagent pack containing the analyte-specific antibody and added to the vessel containing the reaction mixture.

BCI's Access FT4 assay system (BCI, Fullerton, Calif.) is used to measure the concentration of free non-protein bound thyroxine in the serum or plasma of subjects. This assay was first developed using an alkyl amine fluoro-surfactant in the wash solution. The wash solution was used as a probe purge after delivery of the assay reactants and also as a washing solution. In order to substitute the wash solution surfactant with a more environmentally friendly hydrocarbon surfactant, the present invention was developed. The composition of the present invention can contain, but is not limited to, proteins, surfactants, buffer ions, and salt compositions that do not significantly upset the equilibrium of free non-protein bound and protein bound portions of thyroxine in the serum or plasma. Thyroxine binding proteins are comprised of albumin, thyroxine binding globulin, and transthyretin.

In one embodiment of the present invention, EHS is the stabilizing agent and is titrated within an optimized concentration range, in the case for FT4 between about 0.002% volume/volume and about 0.015% volume/volume, preferably at 0.004% volume/volume (or 181 micromolar) in the final reaction composition, to aid in the maintenance of the free to bound equilibrium.

The following examples of how to use the present invention may set forth one or more, but not all, exemplary embodiments of the present invention as contemplated by the inventors, and thus, are not intended to limit the present invention and the scope of the claims in any way.

EXAMPLES

The Access Free T4 assay (BCI) is a two-step enzyme immunoassay. Monoclonal anti-Thyroxine (T4) antibody (BCI) coupled to biotin, a biological sample containing T4, buffered protein solution containing stabilizing agent, and streptavidin-coated solid phase are added to a reaction vessel. During this first incubation the anti-T4 antibody coupled to biotin binds to the solid phase and the free T4 in the sample. After incubation in a reaction vessel, materials bound to the solid phase are held in a magnetic field while unbound materials are washed away. Next, buffered protein solution and triiodothyronine (T3)-alkaline phosphatase conjugate are added to the reaction vessel.

The T3-alkaline phosphatase conjugate binds to the vacant anti-T4 antibody binding sites. After incubation in a reaction vessel, materials bound to the solid phase are held in a magnetic field while unbound materials are washed away. Then, the chemiluminescent substrate Lumi-Phos®530 (Lumigen Inc., Southfield, Mich.) is added to the vessel and light generated by the reaction is measured with a luminometer. The light production is inversely proportional to the concentration of free T4 in the sample. The amount of analyte in the sample is determined from a stored, multi-point calibration curve. Serum and plasma (heparin) are the recommended samples.

BCI's Access Free T4 A33070A assay kit includes an Access Free T4 Reagent Pack Cat. No. 33880: 100 determinations, 2 packs, 50 tests/pack. It is provided ready to use. The reagent pack contains the following Reagents A through E:

Reagent A: Dynabeads® paramagnetic particles coated with streptavidin in a TRIS buffer with protein (ayes), surfactant, 0.125% $NaN_3$, and 0.125% ProClin® 300 (available from Rohm and Haas, Philadelphia, Pa.).

Reagent B: TRIS buffered saline with protein (ayes), surfactant, <0.1% $NaN_3$, and 0.1% ProClin 300.

Reagent C: TRIS buffered saline with protein (ayes), surfactant, 0.125% $NaN_3$, and 0.125% ProClin 300.

Reagent D: Triiodothyronine-alkaline phosphatase (bovine) conjugate in a TRIS buffer with protein (ayes), surfactant, <0.1% $NaN_3$, and 0.1% ProClin 300.

Reagent E: Mouse monoclonal anti-Thyroxine (T4) coupled to biotin in a TRIS buffer with protein (ayes and murine), surfactant and stabilizing agent, 0.125% $NaN_3$, and 0.125% ProClin® 300.

An additional reagent, not part of the reagent pack itself and used for convenience in screening numerous stabilizing agents, is designated as Vial Reagent F. Vial Reagent F is a buffer containing at least one stabilizing agent (for example, sulfonated surfactants as referenced in FIG. 3 or FIG. 4).

Example 1

Stabilizing Agent Only in Reagent E of Reagent Pack

The first reaction comprises the following sequential additions to the reaction vessel:
1) 50 uL of Reagent E (containing stabilizing agent, e.g., 0.016% EHS);
2) 30 uL of analyte-containing sample;
3) 30 uL of system wash buffer (containing no stabilizing agent);
4) 30 uL of Reagent B (containing no stabilizing agent);
5) 50 uL of Reagent A.
   Following incubation and washes of the reaction vessel, the second reaction comprises the following sequential additions to the reaction vessel:
6) 220 uL of Reagent C;
7) 50 uL of Reagent D;
8) 80 uL of system wash buffer (containing no stabilizing agent).
   Following incubation and washes of the reaction vessel, the concentration of the free analyte in the sample is measured using the detection system.

Example 2

Stabilizing Agent Only in Reagent B of Reagent Pack

The first reaction comprises the following sequential additions to the reaction vessel:
1) 50 uL of Reagent E (containing no stabilizing agent);
2) 30 uL of analyte-containing sample;
3) 30 uL of system wash buffer (containing no stabilizing agent);
4) 30 uL of Reagent B (containing stabilizing agent, e.g., 0.016% EHS);
5) 50 uL of Reagent A.
   Following incubation and washes of the reaction vessel, the second reaction comprises the following sequential additions to the reaction vessel:
6) 220 uL of Reagent C;
7) 50 uL of Reagent D;
8) 80 uL of system wash buffer (containing no stabilizing agent).
   Following incubation and washes of the reaction vessel, the concentration of the free analyte in the sample is measured using the detection system.

Example 3

Stabilizing Agent Only in Vial Reagent F of Vial System

The first reaction comprises the following sequential additions to the reaction vessel:
1) 50 uL of Reagent E (containing no stabilizing agent);
2) 30 uL of analyte-containing sample;
3) 30 uL of Vial Reagent F (containing wash buffer with at least one of the stabilizing agents referenced in FIG. 3 or FIG. 4);
4) 30 uL of Reagent B (containing no stabilizing agent);
5) 50 uL of Reagent A.
   Following incubation and washes of the reaction vessel, the second reaction comprises the following sequential additions to the reaction vessel:
6) 220 uL of Reagent C;
7) 50 uL of Reagent D;
8) 80 uL of Vial Reagent F (containing wash buffer with at least one of the stabilizing agents referenced in FIG. 3 or FIG. 4).
   Following incubation and washes of the reaction vessel, the concentration of the free analyte in the sample is measured using the detection system.

Example 4

Stabilizing Agent Only in System Wash Buffer

The first reaction comprises the following sequential additions to the reaction vessel:
1) 50 uL of Reagent E (containing no stabilizing agent);
2) 30 uL of analyte-containing sample;
3) 30 uL of system wash buffer in a salt matrix such as 20 mM TRIS, 0.15M NaCl, 0.1% Proclin 300, 0.1% NaN3, pH 8.0, containing at least one stabilizing agent such as EHS or other sulfonated surfactants as referenced in FIG. 3 or FIG. 4;
4) 30 uL of Reagent B (containing no stabilizing agent);
5) 50 uL of Reagent A.
   Following incubation and washes of the reaction vessel, the second reaction comprises the following sequential additions to the reaction vessel:
6) 220 uL of Reagent C;
7) 50 uL of Reagent D;
8) 80 uL of system wash buffer in a salt matrix such as 20 mM TRIS, 0.15M NaCl, 0.1% Proclin 300, 0.1% NaN3, pH 8.0, containing at least one stabilizing agent such as EHS or other sulfonated surfactants as referenced in FIG. 3 or FIG. 4.

Following incubation and washes of the reaction vessel, the concentration of the free analyte in the sample is measured using the detection system.

These examples illustrate possible embodiments of the present invention. While the invention has been particularly shown and described with reference to some embodiments thereof, it will be understood that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. A kit for use in estimating a concentration of a free thyroid hormone in a sample wherein the thyroid hormone exists in an equilibrium between a free form and a bound form in the sample, the kit comprising:
   (a) a capture ligand for the free thyroid hormone;
   (b) a stabilizing agent that comprises 2-ethyl-hexyl sulfate or salt thereof; and
   (c) a detection system comprising a solid phase coated with a capture ligand-specific binding molecule and an analog of the thyroid hormone labeled with a detectable label capable of specifically binding to said capture ligand.

2. The kit of claim 1 wherein the capture ligand is selected from the group consisting of antibody, antibody fragment, antibody mimic, thyroid hormone binding protein, and combinations thereof.

3. The kit of claim 2 wherein the solid phase is a paramagnetic particle.

4. The kit of claim 2 wherein the capture ligand-specific binding molecule is hapten-specific, and wherein the capture ligand is haptenated.

5. The kit of claim 3 wherein the hapten is biotin.

6. The kit of claim 2 wherein the capture ligand-specific binding molecule is selected from the group consisting of streptavidin, avidin, biotin-specific antibody, biotin-specific antibody fragment, and biotin-specific antibody mimic.

7. The kit of claim 1 wherein the capture ligand is immobilized on a solid phase.

8. The kit of claim 1 wherein the detectable label is alkaline phosphatase.

9. The kit of claim 7 further comprising a chemiluminescent substrate for alkaline phosphatase.

10. The kit of claim 1 wherein the thyroid hormone is selected from the group consisting of thyroxine (T4), triiodothyronine (T3), diiodothyronine (T2), and monoiodothyronine (T1).

11. The kit of claim 1 wherein the detectable label is selected from the group consisting of fluorescent dyes, radiolabels, cofactors, inhibitors, chemiluminescent groups, chromogenic agents, and colorimetric labels.

* * * * *